United States Patent
Watanabe

(10) Patent No.: US 6,410,523 B1
(45) Date of Patent: Jun. 25, 2002

(54) VITAMIN D DERIVATIVES SUBSTITUTED AT THE 2BETA-POSITION

(75) Inventor: Hiroyoshi Watanabe, Tokyo (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/647,874

(22) PCT Filed: Apr. 9, 1999

(86) PCT No.: PCT/JP99/01898
§ 371 (c)(1),
(2), (4) Date: Oct. 6, 2000

(87) PCT Pub. No.: WO99/52863
PCT Pub. Date: Oct. 21, 1999

(30) Foreign Application Priority Data

Apr. 10, 1998  (JP) .............................. 10-137361

(51) Int. Cl.$^7$ ..................... C07C 401/00; A61K 31/593
(52) U.S. Cl. ...................... 514/167; 514/167; 552/653
(58) Field of Search ............................ 514/167; 552/653

(56) References Cited

U.S. PATENT DOCUMENTS 4,666,634 A     5/1987   Miyamoto et al.

FOREIGN PATENT DOCUMENTS

| EP | 0 671 411 A1 | 9/1995 |
| EP | 0 806 413 A1 | 11/1997 |
| JP | 6-340960 | * 12/1994 |
| JP | 8-34769 | * 2/1996 |
| JP | 8-259626 | * 10/1996 |
| WO | 9622973 | * 1/1996 |

OTHER PUBLICATIONS

Ono, Yoshiyuki et al. (CHem. Pharm. Bull., 1997, vol. 45, No. 10, p. 1626–1630).*
Scheddin, Dietmar et al. (Steroids, 1998, vol. 63, Dec., p. 633–643).*

T. Ono et al.; *Synthetic Studies of Vitamin D Analogs. XXIV. Synthesis of Active Vitamin $D_3$ Analogs Substituted at the 2β–Position and Their Preventive Effects on Bone Mineral Loss in Ovariectomized Rats* Chem. Pham. Bull., vol. 45, No. 10, 1997, pp. 1626–1630.

\* cited by examiner

Primary Examiner—Sabiha Qazi
(74) Attorney, Agent, or Firm—Browdy and Neimark

(57) ABSTRACT

The present invention provides a vitamin D derivative of the general formula (I):

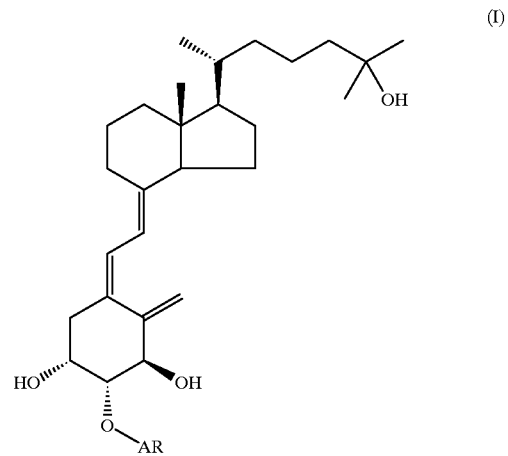

wherein A denotes a straight chain or branched chain alkylene group with 2 to 10 carbon atoms and R denotes $SO_3R_1$ in which $R_1$ represents a hydrogen atom or a straight chain or branched chain alkyl group with 1 to 3 carbon atoms or $COOR_2$ in which $R_2$ represents a hydrogen atom or a straight chain or branched chain alkyl group with 1 to 3 carbon atoms; an intermediate compound for synthesis of the vitamin D derivative; and a pharmaceutical composition containing the vitamin D derivative as an active ingredient. The compound of the invention has affinity for a vitamin D receptor and a vitamin D binding protein, and is useful as a drug, such as a drug for treatment of diseases due to abnormal of calcium metabolism. The compound is considered to be a metabolite of a vitamin D derivative having a substituent at the 2β-position, especially, 2β-(3-hydroxypropoxy)-1α,25-dihydroxyvitamin $D_3$. This compound can advantageously be used as an authentic sample to identify the derivative.

7 Claims, No Drawings

VITAMIN D DERIVATIVES SUBSTITUTED AT THE 2BETA-POSITION

CROSS REFERENCE TO RELATED APPLICATION

The present application is the national stage under 35 U.S.C. 371 of PCT/JP99/01998, filed Apr. 9, 1999.

TECHNICAL FIELD

This invention relates to a vitamin D derivative having a substituent at the 2β-position. More particularly, the invention relates to a vitamin D derivative having at the 2β-position an alkoxy group substituted at the terminal position by $SO_3R_1$ wherein $R_1$ represents a hydrogen atom or a straight chain or branched chain alkyl group with 1 to 3 carbon atoms or by $COOR_2$ wherein $R_2$ represents a hydrogen atom or a straight chain or branched chain alkyl group with 1 to 3 carbon atoms.

BACKGROUND ART

In recent years, vitamin D derivatives have been shown to have various physiological activities. One of vitamin D derivatives, 1α,25-dihydroxyvitamin $D_3$ (1,25$(OH)_2D_3$), is known to show wide varieties of physiological activities, such as calcium metabolism regulating activity, activity of suppressing proliferation, or inducing differentiation, of tumor cells, etc., and immunomodulating activity.

However, 1α,25-dihydroxyvitamin $D_3$ is defective in that it may develop hypercalcemia, depending on its dose or its mode of administration. Using it, for example, as an antitumor agent or an antirheumatic agent poses difficulty. To separate these activities of vitamin D, numerous vitamin D derivatives, such as 1α-hydroxyvitamin $D_3$, 1α, 24-dihydroxyvitamin $D_3$, 22-oxa-1α,25-dihydroxyvitamin $D_3$, and various fluorinated vitamin $D_3$ products, have recently been synthesized, and their physiological activities are under investigation.

Of many vitamin D derivatives, known vitamin $D_3$ derivatives having substituents at the 2β-position include 1α,25-dihydroxy-2β-fluorovitamin $D_3$ described in Japanese Patent Publication No. 1991-14303, vitamin $D_3$ derivatives having at the 2β-position an amino group or a $C_{1-7}$ lower alkoxy group optionally substituted with a hydroxyl group, a halogen atom, a cyano group or an acylamino group (the derivatives described in Japanese Patent Publication No. 1994-23185), and vitamin $D_3$ derivatives having at the 2β-position an optionally substituted lower alkyl, alkenyl or alkinyl group which are described in Japanese Unexamined Patent Publication No. 1994-41059. Some of these vitamin $D_3$ derivatives having substituents at the 2β-position are known to have physiological activities, such as in vivo calcium regulating activity, and activity of inducing differentiation of tumor cells, etc., and also known to be useful as drugs, such as therapeutic agents for diseases due to disorder of calcium metabolism, such as osteoporosis or osteomalacia, or antitumor agents. Of these derivatives, 2β-(3-hydroxypropoxy)-1α, 25-dihydroxyvitamin $D_3$ is expected to be of practical use in treating osteoporosis, with a high blood level being able to be maintained for a long duration.

As noted above, 2β-(3-hydroxypropoxy)-1α, 25-dihydroxyvitamin $D_3$ is under vigorous development as a useful drug, and its metabolites are also under investigation. As studies of such metabolites of 2β-(3-hydroxypropoxy)-1α,25-dihydroxyvitamin $D_3$ are under way, it has been suggested recently that these metabolites appear to include those in which the terminal position of the 3-hydroxypropoxy group at the 2β-position has been converted to a carboxylic acid or a sulfonic acid. However, no reports have been issued on the synthesis of compounds in which the terminal position of the 3-hydroxypropoxy group at the 2β-position of 2β-(3-hydroxypropoxy)-1α, 25-dihydroxyvitamin $D_3$ has been converted to a carboxylic acid or a sulfonic acid.

DISCLOSURE OF THE INVENTION

An object of the present invention is to provide a novel vitamin D derivative having at the 2β-position an alkoxy group substituted at the terminal position by a sulfonic acid or a carboxylic acid or an ester of any of these acids.

Another object of the invention is to provide a novel synthetic intermediate useful for synthesizing the novel vitamin D derivative having at the 2β-position an alkoxy group substituted at the terminal position by a sulfonic acid or a carboxylic acid or an ester of any of these acids; specifically, a steroid compound having at the 2β-position an alkoxy group substituted by a halogen atom at the terminal position.

Still another object of the invention is to provide a drug containing the above-mentioned vitamin D derivative according to the invention as an active ingredient.

In an attempt to attain these objects, the inventor of the present invention used as a starting material a cholestane compound having at the 2β-position an alkoxy group substituted by a hydroxyl group at the terminal position, protected the hydroxyl groups and the 5,7-diene portion that require protection, then converted the terminal hydroxyl group of the substituted alkoxy group at the 2β-(3-position into a nitrile and then into an ester, deprotected the conversion product, and then performed light irradiation and thermal isomerization. By this procedure, the inventor succeeded in synthesizing the desired vitamin D derivative having at the 2β-position an alkoxy group substituted by an ester of a carboxylic acid at the terminal position. The inventor also found this vitamin D derivative to have affinity for a vitamin D receptor and a vitamin D-binding protein, and also to be useful as a drug. These achievements led to accomplishment of the present invention.

According to a first aspect of the invention, here is provided a vitamin D derivative of the general formula (I):

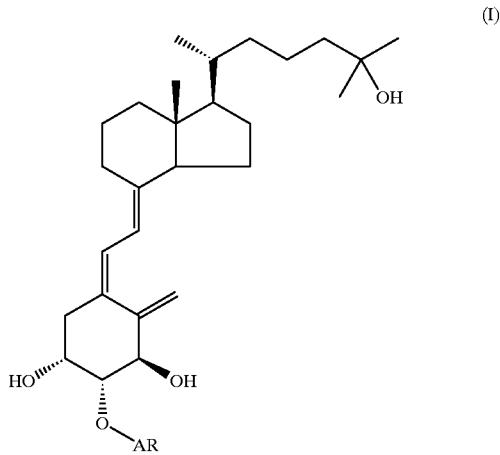

wherein
A denotes a straight chain or branched chain alkylene group with 2 to 10 carbon atoms; and
R denotes
SO₃R₁ in which R₁ represents a hydrogen atom or a straight chain or branched chain alkyl group with 1 to 3 carbon atoms or
COOR₂ in which R₂ represents a hydrogen atom or a straight chain or branched chain alkyl group with 1 to 3 carbon atoms.

In the general formula (I), A is preferably a straight chain alkylene group with 2 to 10 carbon atoms.

In the general formula (I), R is preferably COOR₂ wherein R₂ represents a hydrogen atom or a straight chain or branched chain alkyl group with 1 to 3 carbon atoms.

In the general formula (I), it is particularly preferred that A is an ethane-1,2-diyl group, and R is COOR₂ wherein R₂ represents a hydrogen atom or a straight chain or branched chain alkyl group with 1 to 3 carbon atoms.

Further preferred compounds as the vitamin D derivative of the general formula (I) are 2β-(2-carboxyethyloxy)-1α, 3β,25-trihydroxycholesta-5,7-10(19)-triene and 2β-(2-methoxycarbonylethyloxy)-1α, 3β,25-trihydroxycholesta-5, 7-10(19)-triene.

According to a second aspect of the invention, there is provided a steroid compound of the general formula (II):

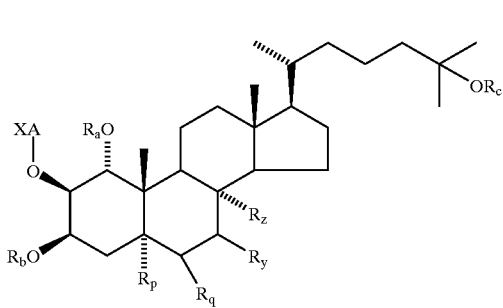

(II)

wherein
A denotes a straight chain or branched chain alkylene group with 2 to 10 carbon atoms;
X denotes a halogen atom;
$R_a$, $R_b$ and $R_c$ denote, independently of each other, a hydrogen atom or a hydroxyl group protecting group; and
$R_p$, $R_q$, $R_y$ and $R_z$ are such that
$R_p$ and $R_q$ together form a double bond between the 5-position and the 6-position and $R_y$ and $R_z$ together form a double bond between the 7-position and the 8-position or
$R_q$ and $R_y$ together form a double bond between the 6-position and the 7-position and R and $R_z$ are bound to a dienophile capable of protecting conjugated double bonds.

This compound is an intermediate compound useful for the synthesis of the vitamin D derivative of the general formula (I).

In the general formula (II), it is preferred that A is a straight chain alkylene group with 2 to 10 carbon atoms, and X is an iodine atom.

According to a third aspect of the invention, there is provided a pharmaceutical composition containing the vitamin D derivative of the general formula (I) as an active ingredient (e.g., a therapeutic agent for a disease due to a disorder of calcium metabolism).

PREFERRED MODES FOR CARRYING OUT THE INVENTION

In defining the vitamin D derivative of the general formula (I), examples of the straight chain or branched chain alkylene group with 2 to 10 carbon atoms, as A, are straight chain alkylene groups which are ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl and decane-1,10-diyl; and branched chain alkylene groups such as 2-methylpropane-1,3-diyl, 2-methylbutane-1,4-diyl, 3-methylbutane-1,4-diyl, 2,3-dimethylbutane-1,4-diyl, 2-methylpentane-1,5-diyl, 3-methylpentane-1,5-diyl, 4-methylpentane-1,5-diyl, 2,3-dimethylpentane-1,5-diyl, 2,4-dimethylpentane-1,5-diyl, 3,3-dimethylpentane-1,5-diyl, 3,4-dimethylpentane-1,5-diyl, 2,3,4-trimethylpentane-1,5-diyl, 3-ethylpentane-1,5-diyl, 3-ethyl-2-methylpentane-1,5-diyl, 3-ethyl-4-methylpentane-1,5-diyl, 2,4-dimethyl-3-ethylpentane-1,5-diyl, 2-methylhexane-1,6-diyl, 3-methylhexane-1,6-diyl, 4-methylhexane-1,6-diyl, 5-methylhexane-1,6-diyl, 2,3-dimethylhexane-1,6-diyl , 2,4-dimethyl hexane-1,6-diyl, 2,5-dimethylhexane-1,6-diyl, 3,3-dimethylhexane-1,6-diyl, 3,4-dimethylhexane-1,6-diyl, 3,5-dimethylhexane-1,6-diyl, 4,4-dimethylhexane-1,6-diyl, 4,5-dimethylhexane-1,6-diyl, 2,3,3-trimethylhexane-1,6-diyl, 2,3,4-trimethylhexane-1,6-diyl, 2,3,5-trimethylhexane-1,6-diyl, 2,4,4-trimethylhexane-1,6-diyl, 2,4,5-trimethylhexane-1,6-diyl, 3,3,4-trimethylhexane-1,6-diyl, 3,3,5-trimethylhexane-1,6-diyl, 3,4,5-trimethylhexane-1,6-diyl, 4,4,5-trimethylhexane-1,6-diyl, 2,3,4,5-tetramethylhexane-1,6-diyl, 3-ethylhexane-1,6-diyl, 4-ethylhexane-1,6-diyl, 3-ethyl-2-methylhexane-1,6-diyl, 3-ethyl-4-methylhexane-1,6-diyl, 3-ethyl-5-methylhexane-1,6-diyl, 4-ethyl-2-methylhexane-1,6-diyl, 4-ethyl-3-methylhexane-1,6-diyl, 4-ethyl-5-methylhexane-1,6-diyl, 2,4-dimethyl-3-ethylhexane-1,6-diyl, 2,5-dimethyl-3-ethylhexane-1,6-diyl, 4,5-dimethyl-3-ethylhexane-1,6-diyl, 2,3-dimethyl-4-ethylhexane-1,6-diyl, 2,5-dimethyl-4-ethylhexane-1,6-diyl, 3,5-dimethyl-4-ethylhexane-1,6-diyl, 3,4-diethylhexane-1,6-diyl, 2-methylheptane-1,7-diyl, 3-methylheptane-1,7-diyl, 4-methylheptane-1,7-diyl, 5-methylheptane-1,7-diyl, 6-methylheptane-1,7-diyl, 2,3-dimethylheptane-1,7-diyl, 2,4-dimethylheptane-1,7-diyl, 2,5-dimethylheptane-1,7-diyl, 2,6-dimethylheptane-1,7-diyl, 3,3-dimethylheptane-1,7-diyl, 3,4-dimethylheptane-1,7-diyl, 3,5-dimethylheptane-1,7-diyl, 3,6-dimethylheptane-1,7-diyl, 4,4-dimethylheptane-1,7-diyl, 4,5-dimethylheptane-1,7-diyl, 4,6-dimethylheptane-1,7-diyl, 5,5-dimethylheptane-1,7-diyl, 5,6-dimethylheptane-1,7-diyl, 2,3,3-trimethylheptane-1,7-diyl, 2,3,4-trimethylheptane-1,7-diyl, 2,3,5-trimethylheptane-1,7-diyl, 2,3,6-trimethylheptane- 1,7-diyl, 2,4,4-trimethylheptane-1,7-diyl, 2,4,5-trimethylheptane-1,7-diyl, 2,4,6-trimethylheptane-1,7-diyl, 2,5,5-trimethylheptane-1,7-diyl, 2,5,6-trimethylheptane-1,7-diyl, 3,3,4-trimethylheptane-1,7-diyl, 3,3,5-trimethylheptane-1,7-diyl, 3,3,6-trimethylheptane-1,7-diyl, 3,4,4-trimethylheptane-1,7-diyl, 3,4,5-trimethylheptane-1,7-diyl, 3,4,6-trimethylheptane-1,7-diyl, 3,5,5-trimethylheptane-1,7-diyl, 3,5,6-trimethylheptane-1,7-diyl, 4,4,5-trimethylheptane-1,7-diyl, 4,4,6-trimethylheptane-1,7-diyl, 4,5,5-trimethylheptane-1,7-diyl, 4,5,6-trimethylheptane-1,7-diyl, 3-ethylheptane-1,7-diyl, 4-ethylheptane-1,7-diyl, 5-ethylheptane-1,7-diyl, 3-ethyl-2-methylheptane-1,7-diyl, 3-ethyl-4-methylheptane-1,7-diyl, 3-ethyl-5-methylheptane-1,7-diyl, 3-ethyl-6-methylheptane-1,7-diyl, 4-ethyl-2-methylheptane-1,7-diyl, 4-ethyl-3-methylheptane-1,7-diyl, 4-ethyl-4-methylheptane-1,7-diyl, 4-ethyl-5- methylheptane-1,7-diyl, 4-ethyl-6-methylheptane-1,7-diyl, 5-ethyl-2-methylheptane-1,7-diyl, 5-ethyl-3-methylheptane-1,7-diyl, 5-ethyl-4-methylheptane-1,7-diyl, 5-ethyl-5-methylheptane-1,7-diyl, 5-ethyl-6-methylheptane-1,7-diyl, 4-n-propylheptane-1,7-diyl, 4-i-propylheptane-1,7-diyl, 2-methyloctane-1,8-diyl, 3-methyloctane-1,8-diyl, 4-methyloctane-1,8-diyl, 5-methyloctane-1,8-diyl, 6-methyloctane-1,8-diyl, 7-methyloctane-1,8-diyl, 2,3-dimethyloctane-1,8-diyl, 2,4-dimethyloctane-1,8-diyl, 2,5-dimethyloctane-1,8-diyl, 2,6-dimethyloctane-1,8-diyl, 2,7-dimethyloctane-1,8-diyl, 3,3-dimethyloctane-1,8-diyl, 3,4-dimethyloctane-1,8-diyl, 3,5-dimethyloctane-1,8-diyl, 3,6-dimethyloctane-1,8-diyl, 3,7-dimethyloctane-1,8-diyl, 4,4-dimethyloctane-1,8-diyl, 4,5-dimethyloctane-1,8-diyl, 4,6-dimethyloctane-1,8-diyl, 4,7-dimethyloctane-1,8-diyl, 5,5-dimethyloctane-1,8-diyl, 5,6-dimethyloctane-1,8-diyl, 5,7-dimethyloctane-1,8-diyl, 6,6-dimethyloctane-1,8-diyl, 6,7-dimethyloctane-1,8-diyl, 3-ethyloctane-1,8-diyl, 4-ethyloctane-1,8-diyl, 5-ethyloctane-1,8-diyl, 6-ethyloctane-1,8-diyl, 2-methylnonane-1,9-diyl, 3-methylnonane-1,9-diyl, 4-methylnonane-1,9-diyl, 5-methylnonane-1,9-diyl, 6-methylnonane-1 9-diyl, 7-methylnonane-1,9-diyl and 8-methylnonane-1,9-diyl. Of these alkylenes, straight chain alkylenes are preferred, and they are ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, and decane-1,10-diyl. More preferred are ethane-1,2-diyl, propane-1,3-diyl, and butane-1,4-diyl. Even more preferred is ethane-1,2-diyl.

Some of the foregoing alkylene groups include those containing an asymmetric carbon atom. The configuration with respect to the asymmetric carbon atom may be R-configuration or S-configuration in the present invention.

As $R_1$ in $SO_3R_1$ as R, a hydrogen atom, a methyl group, an ethyl group, an n-propyl group, and an i-propyl group can be named. Of them, hydrogen and i-propyl are preferred.

As $R_2$ in $COOR_2$ as R, a hydrogen atom, a methyl group, an ethyl group, an n-propyl group, and an i-propyl group can be named. Of them, hydrogen and methyl are particularly preferred.

Examples of the R are a sulfoxyl group, a methoxysulfonyl group, an ethoxysulfonyl group, an n-propoxysulfonyl group, an i-propoxysulfonyl group, a carboxyl group, a methoxycarbonyl group, an ethoxycarbonyl group, an n-propoxycarbonyl group, and an i-propoxycarbonyl group. Of them, a sulfoxyl group, an i-propoxysulfonyl group, a carboxyl group, and a methoxycarbonyl group are preferred, and a carboxyl group, and a methoxycarbonyl group are further preferred.

Typically, preferred examples of AR include an ethane-1,2-diyl group terminally substituted by a sulfoxyl group, an i-propoxysulfonyl group, a carboxyl group or a methoxycarbonyl group, a propane-1,3-diyl group terminally substituted by a sulfoxyl group, an i-propoxysulfonyl group, a carboxyl group or a methoxycarbonyl group, a butane-1,4-diyl group terminally substituted by a sulfoxyl group, an i-propoxysulfonyl group, a carboxyl group or a methoxycarbonyl group, a pentane-1,5-diyl group terminally substituted by a sulfoxyl group, an i-propoxysulfonyl group, a carboxyl group or a methoxycarbonyl group, a hexane-1,6-diyl group terminally substituted by a sulfoxyl group, an i-propoxysulfonyl group, a carboxyl group or a methoxycarbonyl group, a heptane-1,7-diyl group terminally substituted by a sulfoxyl group, an i-propoxysulfonyl group, a carboxyl group or a methoxycarbonyl group, an octane-1,8-diyl group terminally substituted by a sulfoxyl group, an i-propoxysulfonyl group, a carboxyl group or a methoxycarbonyl group, a nonane-1,9-diyl group terminally substituted by a sulfoxyl group, an i-propoxysulfonyl group, a carboxyl group or a methoxycarbonyl group, and a decane-1,10-diyl group terminally substituted by a sulfoxyl group, an i-propoxysulfonyl group, a carboxyl group or a methoxycarbonyl group. Of them, a 2-carboxyethyl group, a 2-methoxycarbonylethyl group, a 3-carboxypropyl group, a 3-methoxycarbonylpropyl group, a 4-carboxybutyl group and a 4-methoxycarbonylbutyl group are particularly preferred, and a 2-carboxyethyl group and a 2-methoxycarbonylethyl group are further preferred.

As the vitamin D derivative of the general formula (I), 2β-(2-carboxyethyloxy)-1α, 3β, 25-trihydroxycholesta-5,7-10(19)-triene, and 2β-(2-methoxycarbonylethyloxy)-1α, 3β, 25-trihydroxycholesta-5,7-10(19)-triene are preferred.

In the definition of the steroid compound of the general formula (II), A is defined as defined in the general formula (I). Examples of the preferred groups, particularly preferred groups, and further preferred groups, as A, are the same as those for the A in the general formula (I).

As X, a chlorine atom, a bromine atom, and an iodine atom are cited. Of them, an iodine atom is preferred.

The hydroxyl group protecting groups in $R_a$, $R_b$ and $R_c$ include, for example, acyl groups such as formyl, acetyl, propionyl, butyryl, isobutyryl, valeryl, isovaleryl, pivaloyl, caproyl, trifluoroacetyl and benzoyl; alkoxycarbonyl groups such as methoxycarbonyl, ethoxycarbonyl, propoxycarbonyl, isopropoxycarbonyl, allyloxycarbonyl, benzyloxycarbonyl and phenoxycarbonyl: substituted silyl groups such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl; substituted methyl groups such as methoxymethyl, methoxyethoxymethyl, methylthiomethyl, t-butylthiomethyl, β-trichloroethyloxymethyl, trimethylsilylethoxymethyl, p-methoxybenzyloxymethyl and p-chlorobenzyloxymethyl; 2-oxacycloalkyl groups such as tetrahydrofuralyl, and tetrahydropyranyl; and aralkyl groups such as benzyl. Of them, substituted silyl groups such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl are preferred. Further, triethylsilyl and t-butyldimethylsilyl are particularly preferred, and triethylsilyl is even more preferred. The $R_a$, $R_b$ and $R_c$ may be the same or different, but are preferably the same.

As the dienophile capable of protecting conjugated double bonds in the definition of $R_p$, $R_q$, $R_y$ and $R_z$, 4-phenyl-1,2,4-triazoline-3,5-dione (PTAD), dimethyl maleate and diethyl maleate are preferred, and 4-phenyl-1,2,4-triazoline-3,5-dione is particularly preferred.

As the steroid compound of the general formula (II), a PTAD adduct of 2β-(2-iodoethyloxy)-1α, 3β,25-tris(triethylsilyloxy)cholesta-5,7-diene is preferred.

The vitamin D derivative of the general formula (I) according to the invention is a novel compound, and can be synthesized, for example, by using 2β-(2-hydroxyethyloxy)-1α, 3β,25-trihydroxycholesta-5,7-diene (compound 1) as a starting material which is described in Japanese Patent Publication No. 1994-23185 (the contents of this publication are all incorporated herein by reference) and performing a method exemplified by the following reaction scheme with the use of desired reagents, where necessary:

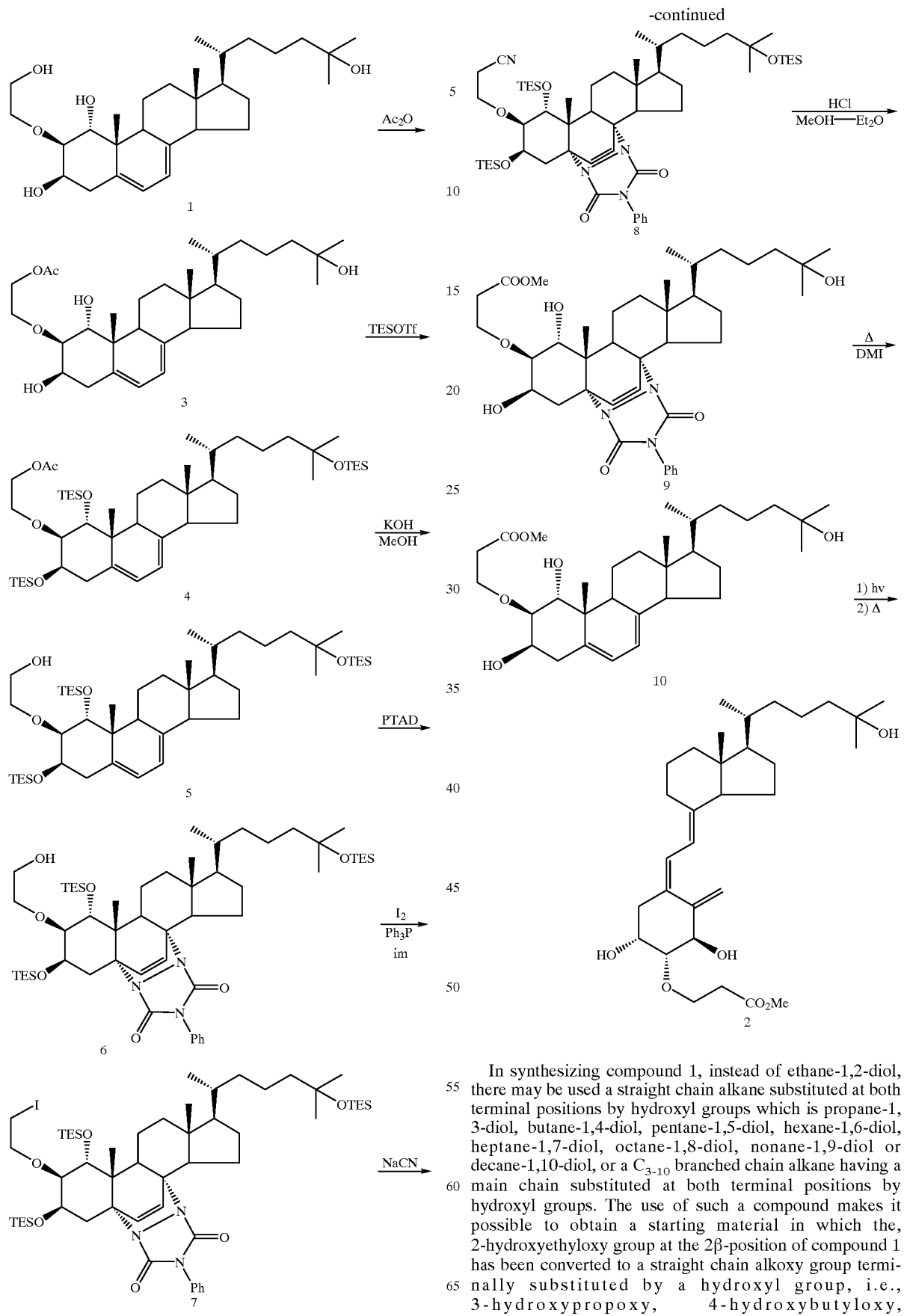

In synthesizing compound 1, instead of ethane-1,2-diol, there may be used a straight chain alkane substituted at both terminal positions by hydroxyl groups which is propane-1,3-diol, butane-1,4-diol, pentane-1,5-diol, hexane-1,6-diol, heptane-1,7-diol, octane-1,8-diol, nonane-1,9-diol or decane-1,10-diol, or a $C_{3-10}$ branched chain alkane having a main chain substituted at both terminal positions by hydroxyl groups. The use of such a compound makes it possible to obtain a starting material in which the 2-hydroxyethyloxy group at the 2β-position of compound 1 has been converted to a straight chain alkoxy group terminally substituted by a hydroxyl group, i.e., 3-hydroxypropoxy, 4-hydroxybutyloxy, 5-hydroxypentyloxy, 6-hydroxyhexyloxy, 7-hydroxyheptyloxy, 8-hydroxyoctyloxy, 9-hydroxynonyloxy or 10-hydroxydecyloxy, or a $C_{3-10}$ branched chain alkoxy group having a main chain terminally substituted by a hydroxyl group.

Alternatively, these starting materials can be synthesized by methods which react epoxide-containing steroid compounds with alcohols under basic conditions as described in Japanese Unexamined Patent Publication No. 1994-340690 (the contents of this publication are all incorporated herein by reference).

Conversion from compound 1 into compound 3 is performed by selectively protecting only the hydroxyl group of the terminal hydroxyalkoxy group at the 2β-position without protecting the hydroxyl groups at the 1α-, 3β- and 25-positions of compound 1. Usable as the protecting group are all groups that can selectively protect only the hydroxyl group of the terminal hydroxyalkoxy group at the 2β-position without substantially adversely affecting the other portions of the molecule and which ensure that the hydroxyl groups at the 1α-, 3β- and 25-positions will not be simultaneously deprotected during deprotection. Of them, an acyl group is preferred. Non-limiting examples of the acyl group are saturated alkylcarbonyl groups such as formyl, acetyl, propionyl, butyryl, isobutyryl, valeryl, isovaleryl, pivaloyl, caproyl, lauroyl, myristoyl, palmitoyl, stearoyl, hydratropoyl, cyclohexanecarbonyl, phenylacetyl and 4-methoxyphenylacetyl; unsaturated alkylcarbonyl groups such as acryloyl, propioloyl, methacryloyl, crotonoyl, isocrotonoyl, oleoyl, elaidoyl, atropoyl and cinnamoyl; and arylcarbonyl groups such as benzoyl, 4-nitrobenzoyl, 4-chlorobenzoyl, 4-methoxybenzoyl, naphthoyl, toluoyl, 3-furoyl, 2-thenoyl, nicotinoyl and isonicotinoyl. Of them, acetyl, propionyl and benzoyl are preferred, and acetyl is further preferred. As an acylating agent, there can be used an acyl halide having any of the above-mentioned groups (the halogen atom of the halide may be chlorine, bromine or iodine), and an acid anhydride having any of the above-mentioned acyl groups. Among them, acetyl chloride, acetic anhydride, propionyl chloride and benzoyl chloride are preferred, and acetic anhydride is further preferred. The base used in the reaction may be an amine such as triethylamine, diisopropylethylamine, pyridine or pyrazine. Preferably, pyridine is used. If desired, a solvent inert to the reaction, such as dichloromethane, may be added. Also, a catalyst for promoting the reaction, such as 4-dimethylaminopyridine (DMAP), may be added, where necessary. The reaction temperature maybe −20 to 60° C., preferably −10 to 10° C. The reaction time may be 0.1 to 36 hours, preferably 1 to 3 hours.

Conversion from compound 3 into compound 4 is performed by protecting the hydroxyl groups at the 1α-, 3β- and 25-positions of compound 3. Usable as the protecting group are all groups that can protect the hydroxyl groups at the 1α-, 3β- and 25-positions at the same time, without substantially adversely affecting the other portions of the molecule. When the protecting group for the hydroxyl group of the terminal hydroxyalkoxy group at the 2β-position is an acy group, a substituted silyl group is preferred. Non-limiting examples of the substituted silyl group are trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl. Of them, triethylsilyl and t-butyldimethylsilyl are preferred, and triethylsilyl is further preferred. The agents for introducing the substituted silyl group may be substituted silyl halides having the above-mentioned groups (the halogen atom of the halide may be chlorine, bromine or iodine), and trifluoromethanesulfonates having the above-mentioned substituted silyl groups. Among them, triethylsilyl chloride, t-butyldimethylsilyl chloride, triethylsilyl trifluoromethanesulfonate and t-butyldimethylsilyl trifluoromethanesulfonate are preferred, and triethylsilyl trifluoromethanesulfonate is further preferred. The base to be used in the reaction may be triethylamine, pyridine, imidazole, or 2,6-lutidine. Preferably, imidazole and 2,6-lutidine are used, and further preferably, 2,6-lutidine is used. If desired, a solvent inert to the reaction, such as tetrahydrofuran (THF), N,N-dimethylformamide, 1,3-dimethyl-2-imidazolidinone (DMI), or dichloromethane, may be added. Also, a catalyst for promoting the reaction, such as 1-hydroxybenzotriazole, maybe added, where necessary. The reaction temperature is not restricted, but is generally −10 to 120° C., preferably −5 to 10° C. The reaction time is not restricted, but is generally 1 to 30 hours, preferably 1 to 3 hours.

Conversion from compound 4 into compound 5 is performed by selectively removing only the hydroxyl group protecting group of the terminal hydroxyalkoxy group at the 2β-position, without removing the hydroxyl group protecting groups at the 1α-, 3β- and 25-positions of compound 4. Usable as the method of deprotection are all methods that can selectively remove only the hydroxyl group protecting groups of the terminal hydroxyalkoxy group at the 2β-position, without substantially adversely affecting the other portions of the molecule and which ensure that the hydroxyl group protecting groups at the 1α-, 3β- and 25-positions will not be simultaneously removed during deprotection. When the hydroxyl group protecting group of the terminal hydroxyalkoxy group at the 2β-position is an acyl group and if the hydroxyl group protecting groups at the 1α-, 3β- and 25-positions are substituted silyl groups, for example, an exemplary applicable method is the hydrolysis of compound 4 with a base. As the base, sodium hydroxide, potassium hydroxide, lithium hydroxide, or barium hydroxide can be used. Preferably, potassium hydroxide is used. As the reaction solvent, water, methanol, ethanol, propanol, tetrahydrofuran, or a mixture of these may be used. Preferably, a mixture of methanol and tetrahydrofuran is used. The reaction temperature may be 0 to 75° C., preferably 10 to 35° C. The reaction time may be 0.5 to 20 hours, preferably 1 to 3 hours. Another applicable example method is by reacting compound 4 with a metal hydride complex compound, such as lithium aluminum hydride, for 1 to 5 hours at a temperature of −10 to 50° C. in a solvent inert to the reaction, such as tetrahydrofuran.

Conversion from compound 5 into compound 6 is performed by protecting the 5,7-diene portion of compound 5. The protecting reagent may be all compounds that can protect the 5,7-diene portion, without substantially adversely affecting the other portions of the molecule. Of them, 4-phenyl-1,2,4-triazoline-3,5-dione, dimethyl maleate and diethyl maleate are preferred, and 4-phenyl-1,2,4-triazoline-3,5-dione is further preferred. Usable as the solvents in the reaction are all solvents that are inert to the reaction and which dissolve both of compound 5 and the above-mentioned protecting reagent. A preferred example of the solvent is dichloromethane. The reaction temperature is not restricted, but is generally 0 to 50° C, preferably 15 to 30° C. The reaction time is not restricted, either but is generally 0.1 to 20 hours, preferably 0.2 to 2 hours.

Conversion from compound 6 into the steroid compound of the general formula (II), in which $R_q$ and $R_y$ together form a double bond between the 6-position and the 7-position, and $R_p$ and $R_z$ are bound to a dienophile capable of protecting conjugated double bonds (e.g., the steroid compound is compound 7), is performed by reacting compound 6 with a halogen in the presence of a base and a phosphine compound to convert the hydroxyl group of the terminal hydroxyalkoxy group at the 2β-position into a halogen atom. As the base, imidazole or benzimidazole can be used. Preferably, imidazole is used. The phosphine compound may be a trialkylphosphine or a triarylphosphine, and preferably, triphenylphosphine is used. As the halogen, iodine is preferably used. Usable as the solvents in the reaction are all solvents that are inert to the reaction and which make the reaction system homogeneous. A preferred example of the solvent is dichloromethane. The reaction temperature may be −5 to 40° C., preferably 15 to 35° C. The reaction time may be 0.5 to 20 hours, preferably 1 to 3 hours.

Subjecting compound 7 to conversion of compound 9 into compound 10 (to be described later on), or a step having an effect comparable to this conversion, gives a steroid compound of the general formula (II) in which $R_p$ and $R_q$ together form a double bond between the 5-position and the 6-position, and $R_y$ and $R_z$ together form a double bond between the 7-position and the 8-position.

Further, compound 7, or a steroid compound of the general formula (II) in which $R_p$ and $R_q$ together form a double bond between the 5-position and the 6-position, and $R_y$ and $R_z$ together form a double bond between the 7-position and the 8-position, is subjected to a customary reaction for elimination of a protecting group (when $R_a$, $R_b$ and $R_c$ are substituted silyl groups, the preferred method is to react the compound with a substituted ammonium fluoride, such as tetra-n-butylammonium fluoride, for a reaction time of 1 to 20 hours at a reaction temperature of 25 to 120° C. with the use of a solvent such as tetrahydrofuran, N,N'-dimethylpropyleneurea, or 1,3-dimethyl-2-imidazolidinone). By this measure, a steroid compound of the general formula (II), in which $R_a$, $R_b$ and $R_c$ are hydrogen atoms, can be obtained. Subjecting this steroid compound to a hydroxyl group protecting reaction known among people skilled in the art can yield a steroid compound of the general formula (II) in which $R_a$, $R_b$ and $R_c$ are each the aforementioned hydroxyl group protecting group, such as an acyl group, an alkoxycarbonyl group, a substituted silyl group, a substituted methyl group, a 2-oxacycloalkyl group, or an aralkyl group.

Conversion from compound 7 into compound 8 is performed by reacting compound 7 with a cyanide compound to convert the halogen atom of the terminal haloalkoxy group at the 2β-position into a cyano group. As the cyanide compound, sodium cyanide or potassium cyanide can be used. Preferably, sodium cyanide is used. The solvent to be used for the reaction may be dimethyl sulfoxide, N,N-dimethylformamide, tetrahydrofuran, or a mixture of these. Preferably, a mixture of dimethyl sulfoxide and tetrahydrofuran is used. The reaction temperature is not restricted, but is generally 0 to 90° C., preferably 20 to 60° C. The reaction time is not restricted, but is generally 1 to 36 hours, preferably 2 to 6 hours.

In the case where the protecting groups of the hydroxyl groups at the 1α-, 3β- and 25-positions of compound 8 are the substituted silyl groups, conversion from compound 8 into compound 9 is performed by reacting compound 8 with an alcohol solution of a hydrogen halide to convert the cyano group of the terminal cyanoalkoxy group at the 23β-position into an alkoxycarbonyl group and simultaneously remove the groups protecting the hydroxyl groups at the 1α-, 3β-and 25-positions. As the hydrogen halide, hydrogen chloride or hydrogen bromide can be used. Preferably, hydrogen chloride is used. The alcohol may be methanol, ethanol, n-propanol, or i-propanol. Preferably, methanol is used. If desired, a solvent inert to the reaction, such as diethyl ether, may be added. The reaction temperature may be 0 to 80° C., preferably 10 to 30° C. The reaction time may be 0.5 to 30 hours, preferably 2 to 10 hours.

Conversion from compound 9 into compound 10 is performed by heating compound 9 in a solvent to remove the protecting group for the 5,7-diene portion, thereby achieving deprotection. The solvent may be dimethyl sulfoxide, N,N-dimethylformamide, or 1,3-dimethyl-2-imidazolidinone. Preferably, 1,3-dimethyl-2-imidazolidinone is used. Where necessary, a reagent for promoting the reaction, such as potassium carbonate, may be added. The reaction temperature is not restricted, but is generally 80 to 155° C., preferably 100 to 150° C. The reaction time is not restricted, either but is generally 0.5 to 15 hours, preferably 0.5 to 3 hours.

Conversion from compound 10 into compound 2 is performed by converting provitamin D to previtamin D, followed by converting previtamin D to vitamin D. Conversion to previtamin D is performed by irradiating provitamin D with ultraviolet rays in a solvent. The solvent may be ethanol, tetrahydrofuran, benzene or toluene, and preferably ethanol or tetrahydrofuran is used. Ultraviolet rays may be natural ultraviolet rays, or artificial ultraviolet rays produced by lamps, etc. Where necessary, ultraviolet light with wavelengths unnecessary for the reaction may be eliminated beforehand with the use of a filter or the like. The reaction temperature may be −20 to 10° C., preferably −5 to 5° C. The reaction time can be varied, as desired, according to the concentration of provitamin D. Generally, the reaction time may be 30 seconds to 7 days.

Subsequent conversion to vitamin D is performed by heating previtamin D in a solvent. The solvent may be ethanol, tetrahydrofuran, benzene or toluene, and preferably ethanol or tetrahydrofuran is used. The reaction temperature may be 0 to 100° C., preferably 4 to 80° C. The reaction time can generally range from 30 minutes to 10 days. If the reaction time exceeds 12 hours, the reaction may be performed with shield from light.

If compound 8 is reacted with a solution of the hydrogen halide in a mixture of alcohol and water when converting compound 8 to compound 9, there can be obtained a compound in which the cyano group of the terminal cyanoalkoxy group at the 2β-position of compound 8 has been converted to a carboxyl group.

If this compound, in which the cyano group of the terminal cyanoalkoxy group at the 2β-position of compound 8 has been converted to a carboxyl group, is subjected to the steps of converting compound 9 to compound 10, and then converting compound 10 to compound 11, or steps comparable in effect to these steps, a compound of the general formula (I) in which R is COOH can be obtained.

If, in the conversion from compound 7 to compound 8, compound 7 or a compound obtained by removing the protecting group of the 5,7-diene portion from compound 7 is reacted with a base-treated methanesulfonic acid ester instead of the cyanide compound, there can be obtained a compound in which the cyano group of compound 8 has been converted to $SO_3R_3$ (wherein $R_3$ denotes a straight chain or branched chain alkyl group with 1 to 3 carbon atoms), or a compound in which the protecting group for the 5,7-diene portion has been removed for deprotection. The base may be n-butyllithium, s-butyllithium, t-butyllithium, phenyllithium, or lithium diisopropylamide, and n-butyllithium and lithium diisopropylamide are preferred. The methanesulfonic acid ester may be methyl methanesulfonate, ethyl methanesulfonate, or i-propyl methanesulfonate. Preferred is i-propyl methanesulfonate. The solvent usable in the reaction is all solvents that are inert to the reaction. The preferred solvents are, for example, diethyl ether and tetrahydrofuran. Where necessary, a solvent effective in promoting the reaction, such as N,N'-dimethylpropyleneurea, may be added. The reaction temperature may be −100 to 0° C., and the reaction time may be 0.5 to 20 hours. Deprotection of the protecting group for the 5,7-diene portion of compound 7 can be performed in the same manner as in the conversion from compound 9 to compound 10.

Further, the compound, in which the cyano group of compound 8 has been converted to $SO_3R_3$ (wherein $R_3$ denotes a straight chain or branched chain alkyl group with 1 to 3 carbon atoms), is subjected to a hydrolysis reaction under acidic conditions which is well known among people skilled in the art, such as a reaction with a hydrous ethanol solution of sulfuric acid at a reaction temperature of 0 to 50° C., this reaction being described in J. Chem. Soc., Perkin Trans. 2, 293–299 (1987). This reaction yields a compound in which the cyano group of compound 8 has been converted to $SO_3H$, or a compound having the cyano group of compound 8 converted to $SO_3H$ and in which at least one of the hydroxyl group protecting groups at the 1α-, 3β-, and 25-positions of the compound has been removed.

Further, the compound in which the cyano group of compound 8 has been converted to $SO_3R_3$ (wherein $R_3$ denotes a straight chain or branched chain alkyl group with 1 to 3 carbon atoms), a compound in which the cyano group of compound 8 has been converted to $SO_3H$, or a compound having the cyano group of compound 8 converted to $SO_3H$ and in which at least one of the hydroxyl group protecting groups at the 1α-, 3β-, and 25-positions of the compound has been removed, is subjected, as necessary, to the step of removing the hydroxyl group protecting groups at the 1α-, 3β-, and 25-positions (in this step, if the hydroxyl group protecting groups at the 1α-, 3β-, and 25-positions are substituted silyl groups, the preferred method is to react the compound with a substituted ammonium fluoride, such as tetra-n-butylammonium fluoride, for a reaction time of 1 to 20 hours at a reaction temperature of 25 to 120° C. with the use of a solvent such as tetrahydrofuran, N,N'-dimethylpropyleneurea, or 1,3-dimethyl-2-imidazolidinone), and then to the step of conversion from compound 9 to compound 10, followed by the step of conversion from compound 10 to compound 11, or to steps comparable in effect to these steps. This procedure gives a compound of the general formula (I) in which R is $SO_3R_1$ (wherein $R_1$ denotes a hydrogen atom, or a straight chain or branched chain alkyl group with 1 to 3 carbon atoms).

The compound of the invention can also be produced by applying the specific manufacturing methods described in the Examples to be offered later on.

The compound of the invention has affinity for a vitamin D receptor and a vitamin D-binding protein, and is useful as a drug, for example, a drug for treatment of diseases due to abnormal calcium metabolism. A pharmaceutical composition containing the compound of the invention as an active ingredient can be administered orally (by ingestion or inhalation) or parenterally (e.g., intravenously, subcutaneously, or topically). For administration, the composition can be formed into a preparation suitable for the mode of administration.

The pharmaceutical composition containing the compound of the invention as the active ingredient can be formed into a preparation by ordinary pharmaceutical manufacturing techniques. Depending on its applications, it can be used as solid and liquid preparations, such as capsules, granules, creams, powders, syrups, tablets, injections, and ointments.

In forming such preparations, nontoxic additives usually used in the pharmaceutical manufacturing of these types of drugs can be used, including stabilizers, lubricants, buffering agents, base materials, flavoring agents, binders, antioxidants, coating agents, colorants, isotonization agents, vehicles, dispersants, disintegrants, preservatives, solvent promoters, and solubilizing agents.

Examples of the stabilizers are sulfites (sodium hydrogensulfite, sodium sulfite, etc.), edetates (sodium edetate, tetrasodium edetate, etc.), hydrogenated oil, sesame oil, sodium chondroitin sulfate, and dibutylhydroxytoluene.

Examples of the lubricants are dried aluminum hydroxide gel, glycerin, silicic acid and its salts (light silicic anhydride, magnesium silicate, etc.), stearic acid and its salts (aluminum stearate, calcium stearate, magnesium stearate, etc.), talc, polyethylene glycol, and phosphoric acid.

Examples of the buffering agents are acetic acid, tartaric acid, sodium carbonate, boric acid, phosphoric acid and its salts (trisodium phosphate, disodium hydrogenphosphate, dipotassium hydrogenphosphate, etc.).

Examples of the base materials are glycerin, vegetable oils (olive oil, sesame oil, wheat germ oil, etc.), stearyl alcohol, cetanol, lard, white petrolatum, paraffin, bentonite, lanolin fatty acid isopropyl ester, and petrolatum.

Examples of the flavoring agents are L-aspartic acid and its salts (monosodium L-aspartate, magnesium L-aspartate, etc.), saccharin sodium, sugars (lactose, sucrose, glucose, D-mannitol, etc.), dl-menthol, and 1-menthols.

Examples of the binders are agar, stearyl alcohol, gelatin, cellulose and its derivatives (ethylcellulose, carboxymethylethylcellulose, hydroxypropylcellulose, hydroxypropylmethylcelluloses, etc.), starch and its derivatives (pregelatinized starch, oxidized starch, dextrin, etc.), sugars (lactose, sucrose, microcrystalline cellulose, glucose, etc.), tragacanth, and polyvinyl alcohol.

Examples of the antioxidants are ascorbic acid, L-ascorbyl stearate, sulfites (sodium sulfite, sodium hydrogensulfite, sodium pyrosulfite, etc.), sodium edetate, erythorbic acid, cysteine hydrochloride, dibutylhydroxytoluene, sodium thiomalate, concentrated mixed tocopherol, butylhydroxyanisole, and propyl gallate.

Examples of the coating agents are shellac, cellulose derivatives (cellulose acetate, hydroxypropylcellulose, cellulose acetate phthalate, hydroxypropylmethylcelluloses, etc.), polyvinyl pyrrolidones, polyethylene glycol, methacrylic acid copolymers, and liquid paraffin.

Examples of the colorants are indigocarmine, caramel, and riboflavin.

Examples of the isotonization agents are potassium chloride, sodium chloride, glycerin, sodium bromide, D-sorbitol, nicotinamide, glucose, and boric acid.

Examples of the vehicles are silicates (synthetic aluminum silicate, magnesium aluminosilicate, calcium silicate, magnesium silicate, etc.), tartaric acid, potassium hydrogentartrate, magnesium hydroxide, cellulose and its derivatives (hydroxypropylcellulose, hydroxypropylmethylcellulose, methylcellulose, etc.), starch and its derivatives (sodium carboxymethyl starch, β-cyclodextrin, dextrin, hydroxypropyl starch, etc.), sugars (lactose, sucrose, glucose, D-mannitol, etc.), glyceryl monostearate, and sorbitan monostearate.

Examples of the dispersants are acacia, propylene glycol alginate, stearic acid and its salts (zinc stearate, magnesium stearate, etc.), sorbitan sesquioleate, D-sorbitol, tragacanth, methylcellulose, and aluminum monostearate.

Examples of the disintegrants are agar, gelatin, cellulose and its derivatives (crystalline cellulose, cellulose acetate phthalate, hydroxypropylcellulose, hydroxypropylmethylcellulose, etc.), carbonates (calcium carbonate, sodium hydrogencarbonate, magnesium carbonate, etc.), starch and its derivatives (sodium carboxymethyl starch, hydroxypropyl starch, etc.), and tragacanth.

Examples of the preservatives are alcohols (chlorobutanol, phenethyl alcohol, propylene glycol, benzyl alcohol, etc.), benzalkonium chloride, benzethonium chloride, dried sodium sulfite, dried sodium sulfate, cresol, chlorocresol, dibutylhydroxytoluene, potassium sorbate, sodium dehydroacetate, parahydroxybenzoate esters (isobutyl parahydroxybenzoate, ethyl parahydroxybenzoate, methyl parahydroxybenzoate, etc.), phenol, formaldehyde, and phosphoric acid.

Examples of the solvent promoters are sodium benzoate, ethylenediamine, citric acid, sodium citrate, glycerin, sodium acetate, sodium salicylate, sorbitan sesquioleate, nicotinamide, glucose, benzyl alcohol, and polyvinylpyrrolidones.

Examples of the solubilizing agents are hydrated silicon dioxide, stearic acid and its salts (calcium stearate, magnesium stearate, etc.), talc, and absolute ethanol.

In addition to these additives, drug components can be added.

The content of the compound of the invention in any of the preparations varies according to the dosage form of the preparation. Generally, it is desired that the compound be contained in a concentration of 0.00001 to 10% by weight. The pharmaceutical composition comprising the compound of the invention can be changed widely according to the type of warm-blooded animals to be treated, including human, the severity of symptoms, diagnosis by the physician, etc. Generally, the content of the compound, as active ingredient, is 0.0000001 to 50 μg/kg/day for oral administration, or 0.000000001 to 10 μg/kg/day for parenteral administration.

The above dose can be administered either at a time or in divided portions once or several times in a day to seven days. The dose can be changed, as required, according to the severity of symptoms, judgment of the physician, etc.

The contents of the specification of Japanese Patent Application No. 1998-137361, the application on the basis of which the present application claims priority are to be incorporated in their entirety by reference.

EXAMPLES

The present invention will be described concretely by way of the following Examples, which in no way limit the invention.

To show the usefulness of the compounds according to the invention, tests were conducted for the affinity of typical compounds of the invention for a vitamin D receptor and a vitamin D binding protein. The results of the tests are shown in Test Example.

Example 1

2β-(2-acetyloxyethyloxy)-1α, 3β, 25-trihydroxycholesta-5,7-diene (compound 3)

To a dichloromethane (30 ml) solution of compound 1 (306 mg, 643 μmol), pyridine (600 μl) and DMAP (10 mg), acetic anhydride (150 μl, 1.59 mmol) was added with ice cooling in an argon atmosphere, and the mixture was stirred for 1.5 hours at the same temperature. The reaction mixture was poured into dilute hydrochloric acid, extracted with dichloromethane, and washed with a saturated solution of sodium carbonate. The organic phase was dried over magnesium sulfate, and then the solvent was distilled off under reduced pressure. The resulting residue was purified by flash column chromatography (ethanol:dichloromethane =0.3:5) to give colorless oily compound 3 (215 mg, 65%), and recover compound 1 (105 mg, 34%). The same procedure was repeated for the recovered compound 1. The resulting products were combined to give compound 3 (260 mg, 79%). $^1$H-NMR: δ0.63(3H, s), 0.96(3H, d, J=6.3 Hz), 1.05 (3H, s), 1.12(6H, s), 2.07(3H, s), 3.64–3.77(2H, m), 3.84 (1H, brs), 3.89–4.00(2H, m), 4.17–4.34(2H, m), 5.33–5.41 (1H, m), 5.70(1H, brd, J=3.6 Hz);

IR(neat)cm$^{-1}$: 3415(br), 2930, 1740;

MS(m/z): 518(M$^+$), 87(100%);

Uvλmax nm: 293, 282, 271.

Example 2

2β-(2-acetyloxyethyloxy)-1α, 3β, 25-tris(triethylsilyloxy)cholesta-5,7-diene (compound 4)

To a dichloromethane (15 ml) solution of compound 3 (260 mg, 502 μmol) obtained in Example 1, and 2,6-lutidine (877 μl, 7.53 mmol), triethylsilyl trifluoromethanesulfonate (1.14 ml, 5.02 mmol) was added with ice cooling in an argon atmosphere, and the mixture was stirred for 1.5 hours at the same temperature. The reaction mixture was concentrated under reduced pressure. The resulting residue was purified by flash column chromatography (5% ethyl acetate/hexane) to give colorless oily compound 4 (327 mg, 76%).

$^1$H-NMR: δ0.52–0.72(21H, m), 0.88–1.03(33H, m), 1.18 (6H, s), 2.04(3H, s), 3.58(1H, brs), 3.63–3.74(1H, m), 3.75(1H, brd, J=3.6 Hz), 3.94–4.11(2H, m), 4.21(2H, t, J=5.0 Hz), 5.28–5.35(1H, m), 5.57–5.62(1H, m);

IR(neat)cm$^{-1}$: 2950, 1750;

MS(m/z): 860(M$^+$), 87(100%);

UV λmax nm: 293, 282, 271.

Example 3

2β-(2-hydroxyethyloxy)-1α, 3β, 25-tris(triethylsilyloxy)cholesta-5,7-diene (compound 5)

To a THF (5 ml) solution of compound 4 (327 mg, 380 μmol) obtained in Example 2, a methanol (10 ml) solution of potassium hydroxide (72 mg, 1.29 mmol) was added, and the mixture was stirred in an argon atmosphere for 1.5 hours at 15 to 30° C. To the reaction mixture, acetic acid (150 μl) was added. Then, the resulting mixture was poured into water, extracted twice with a solvent mixture of ethyl acetate and hexane (1:1), and washed with a saturated solution of sodium carbonate and a saturated aqueous solution of sodium chloride in this order. The organic phase was dried over magnesium sulfate, and then the solvent was distilled off under reduced pressure. The resulting residue was purified by flash column chromatography (8% ethyl acetate/hexane) to give colorless oily compound 5 (173 mg, 56%).

$^1$H-NMR: δ0.51–0.71(21H, m), 0.89–1.07(33H, m), 1.19 (6H, s), 3.48–3.71(4H, m), 3.76(1H, brd, J=3.6 Hz), 3.82–3.91(1H, m), 4.02–4.13(1H, m), 5.30–5.36(1H, m), 5.61(1H, brd, J=5.6 Hz);

IR(neat)cm$^{-1}$: 3465(br), 2955;
MS(m/z): 818(M$^+$), 75(100%);
UV λmax nm: 293, 282, 271.

Example 4

PTAD adduct of 2β-(2-hydroxyethyloxy)-1α, 3β, 25-tris(triethylsilyloxy)cholesta-5,7-diene (compound 6)

To a dichloromethane (15 ml) solution of compound 5 (173 mg, 211 μmol) obtained in Example 3, a dichloromethane (5 ml) solution of PTAD (37 mg, 211 μmol) was added until the reaction mixture turned red, and the mixture was stirred for 30 minutes at 15 to 30° C. The reaction mixture was concentrated under reduced pressure, and the residue was purified by preparative thin-layer chromatography (preparative TLC; 25% ethyl acetate/hexane) to give pale yellow, oily compound 6 (173 mg, 82%).

$^1$H-NMR: δ0.51–0.82(21H, m), 0.89–1.01(30H, m), 1.05 (3H, s), 1.19(6H, s), 3.00(1H, dd, J=13.9, 4.6 Hz), 3.58–3.71 (4H, m), 3.83–3.89(2H, m), 3.91(1H, brd, J=3.0 Hz), 4.90–4.99(1H, m), 6.23(1H, d, J=8.3 Hz), 6.36(1H, d, J=8.3 Hz), 7.23–7.49(5H, m);

IR(neat)cm$^{-1}$: 3580(br), 2950, 1750, 1695;
MS(m/z): 818(M$^+$-PTAD), 103(100%);
UV λmax nm: 258, 218, 206.

Example 5

PTAD adduct of 2β-(2-iodoethyloxy)-1a, 3β,25-tris (triethylsilyloxy)cholesta-5,7-diene (compound 7)

To a dichloromethane (6.7 ml) solution of compound 6 (173 mg, 174 μmol) obtained in Example 4, triphenylphosphine (123 mg, 469 μmol) and imidazole (32 mg, 470 μmol), iodine (75.2 mg, 296 μmol) was added, and the mixture was stirred in an argon atmosphere for 80 minutes at 15 to 30° C. The reaction mixture was poured into a 10% solution of sodium thiosulfate, and extracted twice with dichloromethane. The organic phase was dried over magnesium sulfate, and then the solvent was distilled of f under reduced pressure. The residue was purified by preparative TLC (10% ethyl acetate/hexane) to give colorless oily compound 7 (188 mg, 98%).

$^1$H-NMR: δ0.52–0.73(18H, m), 0.81(3H, s), 0.88–1.01 (30H, m), 1.07(3H, s), 1.19(6H, s), 2.97(1H, dd, J=13.9, 4.6 Hz), 3.20–3.34(2H, m), 3.66(1H, brt, J=3.3 Hz), 3.69–3.81 (1H, m), 3.97(1H, brd, J=3.3 Hz), 4.11–4.22(1H, m), 4.86–4.96(1H, m), 6.23(1H, d, J=8.3 Hz), 6.35(1H, d, J=8.3 Hz), 7.22–7.49(5H, m);

IR(neat)cm$^{-1}$: 2980, 1765, 1715;
MS(m/z): 928(M$^+$-PTAD), 75(100%);
UV λmax nm: 256, 204.

Example 6

PTAD adduct of 2β-(2-cyanoethyloxy)-1α, 3β,25-tris(triethylsilyloxy)cholesta-5,7-diene (compound 8)

To a solution, in dimethyl sulfoxide (26 ml) and THF (15 ml), of compound 7 (180 mg, 163 μmol) obtained in Example 5, a dimethyl sulfoxide (8 ml) solution of sodium cyanide (8.0 mg, 163 μmol) was added, and the mixture was stirred in an argon atmosphere for 3.5 hours at 50° C. The reaction mixture was poured into ice water, extracted twice with a solvent mixture of ethyl acetate and hexane (10:1), and washed once with water. The organic phase was dried over magnesium sulfate, and then the solvents were distilled off under reduced pressure. The residue was purified by preparative TLC (15% ethyl acetate/hexane) to give colorless oily compound 8 (141 mg, 87%).

$^1$H-NMR: δ0.51–0.75(18H, m), 0.80(3H, s), 0.89–1.02 (30H, m), 1.05(3H, s), 1.19(6H, s), 2.98(1H, dd, J=13.9, 4.6 Hz), 3.66(1H, brt, J=3.3 Hz), 3.71–3,79(1H, m), 3.93(1H, brd, J=3.0 Hz), 4.06–4.13(1H, m), 4.90–4.98(1H, m), 6.23 (1H, d, J=8.3 Hz), 6.35(1H, d, J=8.3 Hz), 7.22–7.49(5H, m);

IR(neat)cm$^{-1}$: 2955, 2250, 1750, 1700;
MS(m/z): 827(M$^+$-PTAD), 75(100%);
UV λmax nm: 258, 204.

Example 7

PTAD adduct of 2β-(2-methoxycarbonylethyloxy)-1α, 3β, 25-trihydroxycholesta-5,7-diene (compound 9)

To a diethyl ether (6.6 ml) solution of compound 8 (75 mg, 74.9 μmol) obtained in Example 6, a methanol solution of hydrogen chloride gas (3.3 ml, corresponding to 735 mg of hydrogen chloride) was added, and the mixture was stirred in an argon atmosphere for 6.5 hours at 15 to 30° C. The reaction mixture was concentrated under reduced pressure, and the residue was purified by preparative TLC (ethanol:dichloromethane =1:10) to give colorless oily compound 9 (13 mg, 25%).

$^1$H-NMR: δ0.80(3H, s), 0.96(3H, d. J=6.3 Hz), 1.00(3H, s), 1.21(6H, s), 2.59(2H, t, J=5.6 Hz), 3.08–3.18(1H, m), 3.70(3H, s), 3.78–3.98(4H, m), 4.68–4.78(1H, m), 6.20(1H, d, J=8.3 Hz), 6.40(1H, d, J=8.3 Hz), 7.25–7.42(5H, m);

IR(neat)cm$^{-1}$: 3445(br), 2950, 1740, 1690;
MS(m/z): 518(M$^+$-PTAD), 60(100%).

Example 8

2β-(2-methoxycarbonylethyloxy)- 1α, 3β,25-trihydroxycholesta-5,7-diene (compound 10)

A DMI (3 ml) solution of compound 9 (18 mg, 26.0 μmol) obtained in Example 7 was stirred in an argon atmosphere for 1 hour at 140° C. The reaction mixture was left to cool, and then poured into water. The mixture was extracted twice with a solvent mixture of ethyl acetate and hexane (4:1), and washed with water twice. The organic phase was dried over magnesium sulfate, and then the solvents were distilled off under reduced pressure. The residue was purified by preparative TLC (1% ethanol/ethyl acetate) to give white powdery compound 10 (8 mg, 59%).

$^1$H-NMR: δ0.63(3H, s), 0.96(3H, d, J=6.6 Hz), 1.00(3H, s), 1.20(6H, s), 2.61(2H, t, J=5.8 Hz), 3.64–3.85(4H, m), 3.74(3H, s), 3.90–4.01(1H, m), 5.31–5.39(1H, m), 5.62–5.69(1H, m);

IR(KBr)cm$^{-1}$: 3420(br), 2960, 1725;
MS(m/z): 518(M$^+$), 60(100%);
UV λmax nm: 294, 282, 271.

Example 9

2β-(2-methoxycarbonylethyloxy)-1α, 3β,25-trihydroxy-9,10-secocholesta-5,7,10(19)-triene (compound 2)

An ethanol (200 ml) solution of compound 10 (8 mg, 15.4 μmol) obtained in Example 8 was irradiated with light for 95 seconds with the use of a 400 W high pressure mercury lamp-Vycor filter, with ice cooling and under bubbling with an argon gas. Then, the irradiated solution was heated under reflux for 2 hours. The solvent was distilled off under reduced pressure, and the residue was purified by preparative TLC (1% ethanol/ethyl acetate) to give white foamy compound 2 (2 mg, 25%).

$^1$H-NMR: δ0.55(3H, s), 0.93(3H, d, J=6.3 Hz), 1.22(6H, s), 2.66(2H, t, J=5.1 Hz), 3.26(1H, dd, J=9.1, 2.8 Hz), 3.73(3H, s), 3.74–3.83(1H, m), 3.92–4.02(1H, m), 4.24–4.32(2H, m), 5.08(1H, s), 5.53(1H, s), 6.06(1H, d, J=11.4 Hz), 6.36(1H, d, J=11.4 Hz);

IR(neat)cm$^{-1}$: 3460(br), 2925, 1735;
MS(m/z): 518(M$^+$), 60(100%);
UV λmax nm: 264, min nm: 229.

Test Example

Compound 2 of the present invention was evaluated for affinity for a chick small intestine vitamin D receptor and a rat plasma vitamin D binding protein in comparison with 1α,25-dihydroxyvitamin $D_3$ or 25-hydroxyvitamin $D_3$.

Specifically, a $^3$H-1α,25-dihydroxyvitamin $D_3$ solution (to test affinity for a chick small intestine vitamin D receptor) or a $^3$H-25-hydroxyvitamin $D_3$ solution (to test affinity for a rat plasma vitamin D binding protein) was mixed with a solution of a test compound (1α,25-dihydroxyvitamin $D_3$, 25-hydroxyvitamin $D_3$, or compound 2) at various concentrations. A solution of a chick small intestine vitamin D receptor, or a solution of a rat plasma vitamin D binding protein was added, and the resulting mixture was left to stand. Then, a dextran coated charcoal solution was added, and the mixture was left to stand in ice cooling, and centrifuged. To the supernatant, a liquid scintillator was added, and the mixture was measured for radioactivity. $B/B_0$ (B=the value of radioactivity measured upon addition of the test compound, $B_0$=the value of radioactivity measured without addition of the test compound) was calculated to find the concentration of the test compound at which $B/B_0$=0.5. The results are shown in Tables 1 and 2.

TABLE 1

Comparative Experiments on Affinity of Vitamin D Derivatives for Chick Small Intestine Vitamin D Receptor

|  | 1,25-Dihydroxyvitamin $D_3$ | Compound 2 |
|---|---|---|
| 50% binding ability (ng) | 0.046 | 0.455 |
| Ratio | 1 | 1/9.9 |

(50% binding ability refers to the amount of the test compound providing $B/B_0$=0.5)

TABLE 2

Comparative Experiments on Affinity of Vitamin D Derivatives for rat plasma vitamin D binding protein

|  | 25-Hydroxyvitamin $D_3$ | 1,25-Dihydroxyvitamin $D_3$ | Compound 2 |
|---|---|---|---|
| 50% binding ability (ng) | 0.209 | 27 | 4 |
| Ratio | 129 | 1 | 1/6.8 |

(50% binding ability refers to the amount of the test compound providing $B/B_0$=0.5)

As shown in Tables 1 and 2, the compound of the present invention has affinity for a vitamin D receptor and a vitamin D binding protein.

Industrial Applicability

The compound of the present invention has affinity for a vitamin D receptor and a vitamin D binding protein, and is useful as a drug, for example, a drug for treatment of diseases due to abnormal calcium metabolism. The compound is considered to be a metabolite of a vitamin D derivative having a substituent at the 2β-position, especially, 2β-(3-hydroxypropoxy)-1α,25-dihydroxyvitamin $D_3$. This compound can advantageously be used as an authentic sample to identify the derivative.

What is claimed is:

1. A vitamin D derivative of the general formula (I):

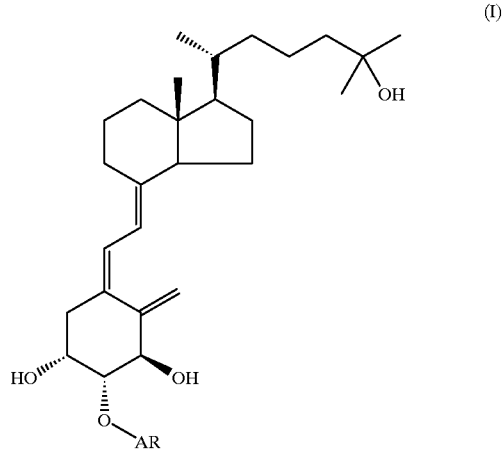

wherein

A denotes a straight chain or branched chain alkylene group with 2 to 10 carbon atoms; and R denotes $SO_3R_1$ in which $R_1$ represents a hydrogen atom or a straight chain or branched chain alkyl group with 1 to 3 carbon atoms or $COOR_2$ in which $R_2$ represents a hydrogen atom or a straight chain or branched chain alkyl group with 1 to 3 carbon atoms.

2. A vitamin D derivative as claimed in claim 1, wherein A is a straight chain alkylene group with 2 to 10 carbon atoms.

3. A vitamin D derivative as claimed in claim 1, 2, wherein R is $COOR_2$ in which $R_2$ represents a hydrogen atom or a straight chain or branched chain alkyl group with 1 to 3 carbon atoms.

4. A vitamin D derivative as claimed in claim 1, wherein A is an ethane-1,2-diyl group; and R is $COOR_2$ in which $R_2$ represents a hydrogen atom or a straight chain or branched chain alkyl group with 1 to 3 carbon atoms.

5. A vitamin D derivative as claimed in claim 1, which is selected from 2β-(2-carboxyethyloxy)-1α, 3β,25-trihydroxycholesta-5,7-10(19)-triene and 2β-(2-methoxycarbonylethyloxy)-1α, 3β,25-trihydroxycholesta-5, 7-10(19)-triene.

6. A pharmaceutical composition containing a vitamin D derivative, as claimed in claim 1, as an active ingredient.

7. A pharmaceutical composition as claimed in claim 6, which is a drug for treatment of diseases due to abnormal calcium metabolism.

\* \* \* \* \*